United States Patent
Baker

[11] Patent Number: 6,126,658
[45] Date of Patent: Oct. 3, 2000

[54] RADIOFREQUENCY MEDICAL INSTRUMENT AND METHODS FOR VESSEL WELDING

[76] Inventor: James A. Baker, 4292-P Wilkie Way, Palo Alto, Calif. 94306

[21] Appl. No.: 09/251,860

[22] Filed: Feb. 17, 1999

Related U.S. Application Data

[60] Provisional application No. 60/075,275, Feb. 19, 1998.
[51] Int. Cl.[7] .................................................. A61B 18/14
[52] U.S. Cl. .............................. 606/51; 606/38; 606/40; 606/52
[58] Field of Search .................................. 606/45, 46, 48, 606/49–52, 38, 40

[56] References Cited

U.S. PATENT DOCUMENTS

| | | | |
|---|---|---|---|
| 5,151,102 | 9/1992 | Kamiyama et al. | 606/51 |
| 5,269,780 | 12/1993 | Roos | 606/51 |
| 5,290,287 | 3/1994 | Boebel et al. | 606/51 |
| 5,403,312 | 4/1995 | Yates et al. | 606/50 |
| 5,443,463 | 8/1995 | Stern et al. | 606/51 |
| 5,693,051 | 12/1997 | Schulze et al. | 606/51 |
| 5,702,390 | 12/1997 | Austin et al. | 606/48 |
| 5,833,690 | 1/1998 | Yates et al. | 606/51 |
| 5,891,141 | 4/1999 | Rydell | 606/51 |
| 6,039,733 | 3/2000 | Buysse et al. | 606/40 |

*Primary Examiner*—Lee Cohen
*Attorney, Agent, or Firm*—Fish & Neave; Nicola A. Pisano

[57] ABSTRACT

Methods and apparatus are provided for welding or sealing vessels or organs by collapsing a vessel with a jaw-like structure, applying an RF current between first and second bi-polar electrodes, and directing path of the RF current using a channeling electrode disposed intermediate the first and second bi-polar electrodes. The jaw-structure may be configured to progressively collapse the section of tissue to may squeeze fluids out of the lumen of the vessel. In addition, the jaw-structure may be configured to elongated the collapsed section of vessel to alter its impedance characteristics prior to application of RF energy. The device also may include one or more sensors providing signals to a power controller that modulates application of RF energy to the vessel.

20 Claims, 8 Drawing Sheets

RADIOFREQUENCY MEDICAL INSTRUMENT AND METHODS FOR VESSEL WELDING

REFERENCE TO RELATED APPLICATIONS

This application claims priority from U.S. Provisional Pat. application Ser. No. 60/075,275, filed Feb. 19, 1998. This application also is related to U.S. Pat. application Ser. No. 08/920,291, filed Aug. 28, 1997, now U.S. Pat. No. 5,957,920, and Ser. No. 09/191,413, filed Nov. 12, 1998, which are hereby incorporated herein by reference.

FIELD OF THE INVENTION

This invention relates to methods and apparatus for utilizing RF energy to seal tubular vessels of organs, and more particularly for delivering RF energy in a controlled manner to denature proteins in the endothelial tissues to form a thermal biological weld to close the vessel or organ.

BACKGROUND OF THE INVENTION

In both open and endoscopic surgeries, it often is necessary to seal or weld blood vessels, both veins and arteries, ranging in size from less than 1 mm in diameter to more than 6 mm in diameter. For example, in subfacial endoscopic perforator surgery or SEPS, a series of perforator vessels in a patient's leg are sealed closed to alleviate venous ulcerations. In a typical SEPS procedure, the surgeon uses a mechanically deformable clip to pinch off such perforator vessels. A single clip may not seal a vessel in a reliable manner and the surgeon typically uses multiple clips on each perforator vessel to assure an effective seal. It would be preferable to seal a vessel without leaving a metal clip implanted in the patient's body.

Radio frequency ("RF") instruments for sealing blood vessels have been developed. An example of a previously known bi-polar grasper, shown in FIG. 1A, typically applies from 40 watts to 100 watts or more of power to the exterior of a vessel to cauterize such vessels or vascularized tissue masses. To use such previously known bi-polar instruments, a blood vessel is squeezed between the opposing (first and second) jaw faces of the grasper (see FIG. 1B). Each jaw face comprises a conductive electrode (first electrode 2A and second electrode 2B) and when operating in a bi-polar fashion, the RF current generally flows directly "across" vessel 3 indicated by the arrow in FIG. 1B from the first electrode 2A to the second electrode 2B or vice versa.

Additionally, there may be stray RF current flow in circuitous low resistance routes, e.g., outwardly along the vessel and then through surrounding tissue, to reach the other electrode. This type of stray RF current flow is undesirable. For example, in a SEPS procedure or when sealing a branch vein of any arterial conduit that may be mobilized for a bypass, it is undesirable to have stray RF current affect the arterial conduit.

In using a previously known device such as depicted in FIGS. 1A–1B, the impedance of the tissue of the vessel wall changes continuously during the application of RF, making sealing erratic. The high levels of power typically used in previously known devices (e.g., 40 to 100 watts), makes the tissue impedance levels undesirably change very rapidly. At power levels ranging from 40 to 100 watts, impedance levels typically will increase within a few seconds to a level such that RF energy flow is impeded or restricted altogether, and may contribute to an increase in stray RF current. Moreover, the vessel walls often will not be fused together over a sufficient area to provide an effective seal.

Furthermore, previously known devices, such as shown in FIGS. 1A–1B, which simply clamp the vessel walls together, often entrap blood between the luminal surfaces. This trapped blood acts as a heat sink and may adversely affect the uniformity of RF thermal effects. It has been observed that the entrapment of blood within the lumen significantly interferes with the binding characteristics of the denatured proteins that are created and that comprise the amalgam for fusing the vessel walls together.

It would therefor be desirable to provide an RF energy delivery system, and methods of use, that reduce the unwanted effects of variable tissue impedance, thereby allowing an effective energy delivery profile in the tissue targeted for welding.

It also would be desirable to provide an RF energy delivery system, and methods of use, wherein an openable/closeable jaw structure reduces the risk of entrapping blood between the vessel walls.

It further would be desirable to provide an RF energy delivery system, and methods of use, that reduce tissue charring and smoke, which can obscure the physician's view, particularly in endoscopic surgeries.

It still further would be desirable to provide an RF energy delivery system, and methods of use, that reduce the outward spread of thermal effects along a vessel (e.g., to protect a main vessel when sealing branch vessels close to main vessel).

It also would be desirable to provide an RF energy delivery system, and methods of use, that substantially reduce stray RF currents from traveling outwardly along a vessel away from the portion targeted for welding.

SUMMARY OF THE INVENTION

In view of the foregoing, it is an object of this invention to provide an RF energy delivery system, and methods of use, that reduce the unwanted effects of variable tissue impedance, thereby allowing an effective energy delivery profile in the tissue targeted for welding.

It is also an object of this invention to provide an RF energy delivery system, and methods of use, wherein an openable/closeable jaw structure reduces the risk of entrapping blood between the vessel walls.

It is a further object of the present invention to provide an RF energy delivery system, and methods of use, that reduce tissue charring and smoke, which can obscure the physician's view, particularly in endoscopic surgeries.

It is another object of this invention to provide an RF energy delivery system, and methods of use, that reduce the outward spread of thermal effects along a vessel (e.g., to protect a main vessel when sealing branch vessels close to main vessel).

It still further is an object of this invention to provide an RF energy delivery system, and methods of use, that substantially reduce stray RF currents from traveling outwardly along a vessel away from the portion targeted for welding.

These and other objects of the present invention are accomplished by providing apparatus and methods for applying RF energy to tissue that (1) progressively engage a vessel or organ to minimize the amount of blood entrapped in the lumen, and thereafter maintains the vessel walls in close approximation under appropriate pressures for welding; (2) delivers bi-polar RF energy longitudinally along the length of the vessel to create an effective seal; (3) directs the path of the RF current along the vessel lumen; and optionally (4) stretches the targeted vessel segment prior to application of the RF energy to alter its impedance characteristics.

A preferred embodiment of an instrument of the present invention comprises an introducer member that carries a distal working end with an openable/closeable jaw structure for engaging a targeted vessel section. The jaw structure is moveable between an open position and a closed position by a suitable mechanism disposed in a handle portion coupled to the introducer member. The jaw structure has an upper jaw side or member and a lower jaw side or member with cooperating opposing jaw faces.

Each jaw face defines right-side and left-side portions that cooperate with portions of the opposing jaw face. The upper jaw side includes a central projecting portion. The lower jaw has deflectable right-side and left-side elements with a central receiving structure or gap for receiving the opposing side's projecting portion. The cooperating jaw faces (projecting and receiving portions) serve several purposes.

First, the deflectable right-side and left-side elements of the lower jaw face deflect outward when the jaws close to progressively engage the vessel from the center of the targeted vessel section and cause blood within the lumen to be squeezed out of the targeted area. Second, the deflectable receiving jaw elements may be designed to stretch the vessel before RF delivery to alter the impedance characteristics of the targeted vessel section. Also, the deflectability of the right-side and left-side elements in the closed position allows the jaw structure to accommodate vessels of different diameters and maintain the luminal surfaces (when collapsed) within a particular pressure range that is suitable for an RF-induced thermal biological weld.

In accordance with the principles of the present invention, the jaw structure carries an electrode configuration that allows RF energy delivery at very low power levels (0.50 to 30.0 watts), yet creates thermal effects sufficient to weld luminal tissues. First and second bi-polar electrodes disposed on the right-side and left-side portions of the jaw assembly provide a flow of current longitudinally through the targeted vessel section. One or more non-active "channeling" electrodes, i.e., that are insulated from the first and second bi-polar electrodes and the RF power supply, are positioned intermediate to the first and second bi-polar electrodes. Optionally, a thermal sensor or sensor array may be provided to measure temperatures of the section of the vessel targeted for welding, contemporaneous with RF energy delivery.

A preferred method of the present invention for welding closed the lumen of a blood vessel or organ comprises: (1) delivering an RF current along a vessel section between first and second spaced-apart bi-polar electrodes; and (2) directing the RF current between the first and second electrodes through a path in tissue generally proximate to an intermediate channeling electrode that is in longitudinal contact with the vessel section.

Optionally, prior to application of the RF current, the vessel may be progressively engaged by first engaging a center section and then pushing blood outwardly from the vessel lumen toward the first and second ends of the vessel section. Alternatively, or in addition, the impedance characteristics of the vessel section targeted for welding may be altered by stretching or extending the targeted vessel section to alter the extracellular fluid ("ECF") content level of the vessel wall and endothelium.

BRIEF DESCRIPTION OF THE DRAWINGS

Additional objects and advantages of the invention will be apparent from the following description, the accompanying drawings and the appended claims, in which:

DETAILED DESCRIPTION OF THE INVENTION

Figure 1A:
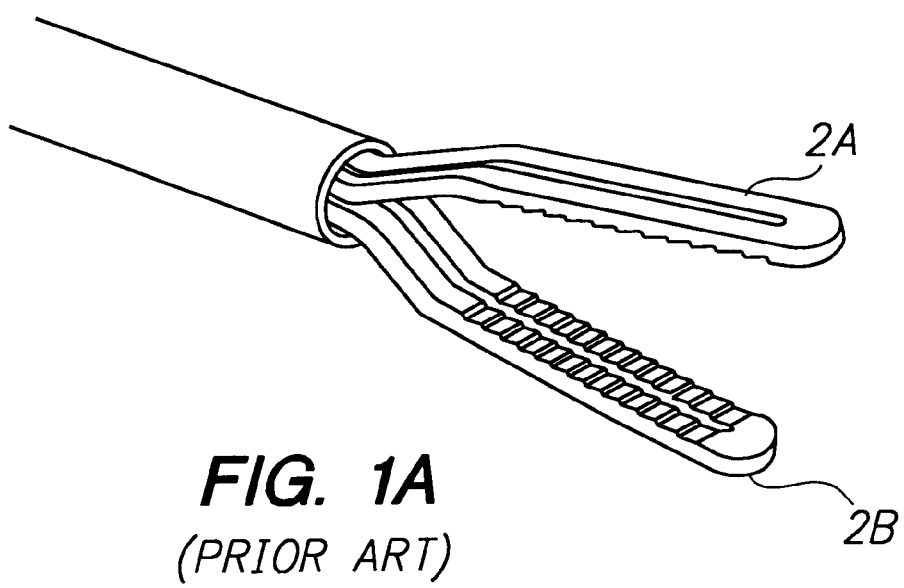
FIGS. 1A–1B are perspective views of a jaw structure of a previously known bi-polar radiofrequency device and its use in cautery.

The present invention provides apparatus and methods for controlling the effects of RF energy delivery to a blood vessel captured within a working end of an instrument to improve RF energy delivery profiles for welding small and large blood vessels (or other organs) quickly and efficiently.

The apparatus and methods of the present invention may be used to seal or weld blood vessels in a number of different procedures. For purposes of illustration, the present invention is described for use in performing subfacial endoscopic perforator surgery (SEPS). In this disclosure, the term blood vessel is defined to include any artery or vein of any size, and further includes tissue/vessel combinations or vascularized tissue masses where an individual vessel cannot be separated from the tissue. The apparatus and methods of the present invention also find application in sealing the lumens of other organs or anatomic structures having lumens with collagen-containing tissues capable of forming biological glue.

It is known that many beneficial results, such as the reduction of charring, smoke, and stray RF current, may be achieved by reducing RF power levels. In accordance with the principles of the present invention, RF power levels may be reduced to 0.50 watts to 30.0 watts and still achieve the significant thermal effects required to weld tissue.

The mechanism of tissue welding is complex and is not well understood. The application of RF energy to tissue results in heat which denatures tissue proteins in the vessel walls and in the endothelial lining of the vessel, which includes a type of collagen. The heat denatures the proteins in the collagen-containing tissues into a proteinaceous amalgam, which forms a thermal biological glue in a temperature range from 65° C. to 90° C. The integrity of the sealing effect depends greatly on the conductive characteristics of the target tissue, which in turn effect denaturation of proteins.

To form an effective seal, it is necessary to maintain a desired temperature over the targeted vessel section for an appropriate time period to develop a uniform layer of denatured proteins. Even partial denaturation of the endothelial lining involves disruption of cellular membranes, thereby allowing cellular fluids and extracellular matrix materials to intermix. The resultant thermally elevated amalgam of denatured proteins bind together to create a biological weld. When the source of thermal energy is removed, the proteins re-nature and fuse the luminal walls. As the vessel heals over time, the biological weld is reabsorbed by the body via the wound healing process.

Several variables come into play when using RF energy to elevate luminal tissues to the levels required to denature proteins. For purposes of the present invention, the energy source may be a previously known RF generator operating with a high frequency alternating current (e.g., from 50,000 Hz to 500,000 Hz) that is adapted to flow from (or between) one or more electrodes through the vessel walls targeted for welding. As is known, the application of such alternating current causes ionic agitation and friction in the targeted tissue as ions (generally within extracellular matrices and not within intracellular fluids) follow the changes in direction of the alternating current. Such ionic agitation or frictional heating does not result from direct tissue contact with a thermally-elevated electrode.

In the delivery of energy to a tissue mass, I=E/R, where I is the intensity of the current in amperes, E is the energy potential measured in volts and R is the tissue resistance measured in ohms. Current density, or the level of current intensity, is an important gauge of energy delivery, and relates to the impedance of the targeted tissue mass. The level of heat generated within the target tissue thus is influenced by several factors, such as (i) RF current intensity, (ii) RF current frequency, (iii) impedance levels within the targeted tissue disposed between the electrodes, which vary during treatment a treatment cycle, (iv) heat dissipation from the targeted tissue; (v) duration of RF energy delivery, and (vi) distance traveled through the targeted tissue by the RF current between the conductive electrodes.

Figure 2A:
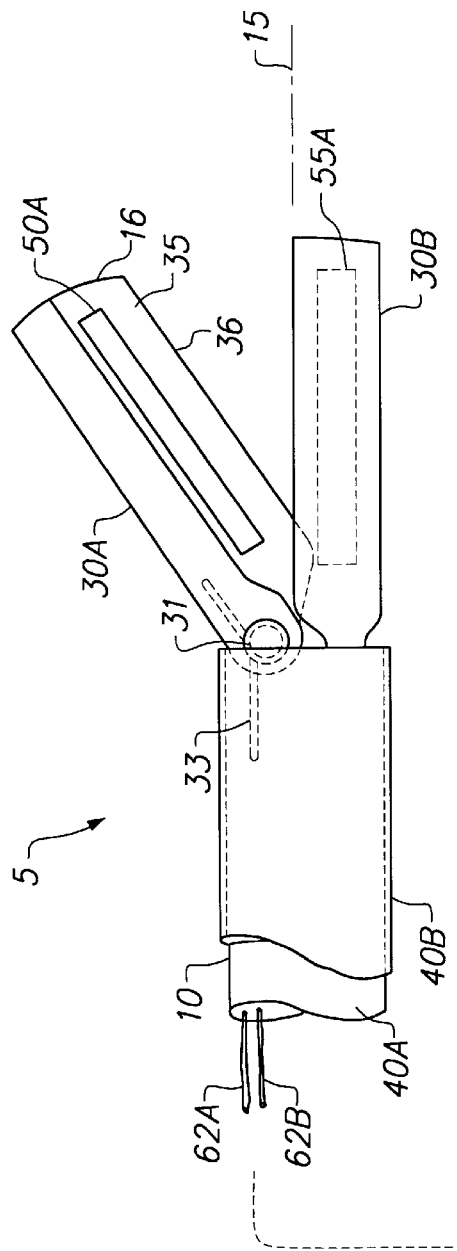
FIGS. 2A–2B are, respectively, plan views of the jaw structure of the present invention with the jaw sides in the open and closed positions.
Figure 2B:
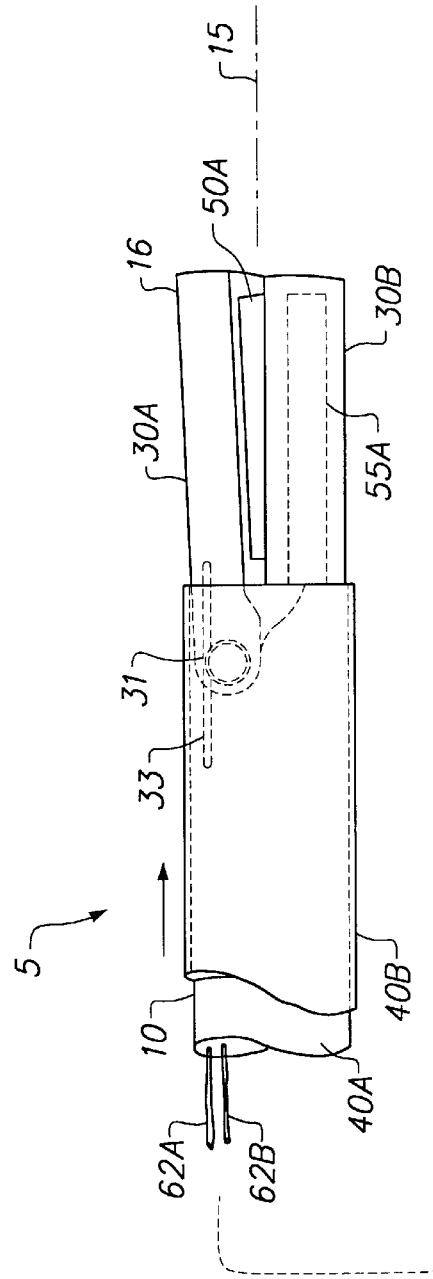

Referring now to FIGS. 2A–2B, a preferred embodiment of instrument 5 constructed in accordance with the present invention is described. Instrument 5, which is adapted for open or endoscopic procedures with handle portion 7 (see FIG. 6A), is coupled to elongate introducer portion 10 extending along axis 15 and carrying distal working end 16. Introducer portion 10 illustratively has a cylindrical cross-section and is made of suitable biocompatible materials, such as metal or plastic. Introducer portion 10 preferably has an outer diameter of ranging from 5 mm to 10 mm, e.g., to cooperate with a standard endoscopic trocar sleeve.

Figure 3A:
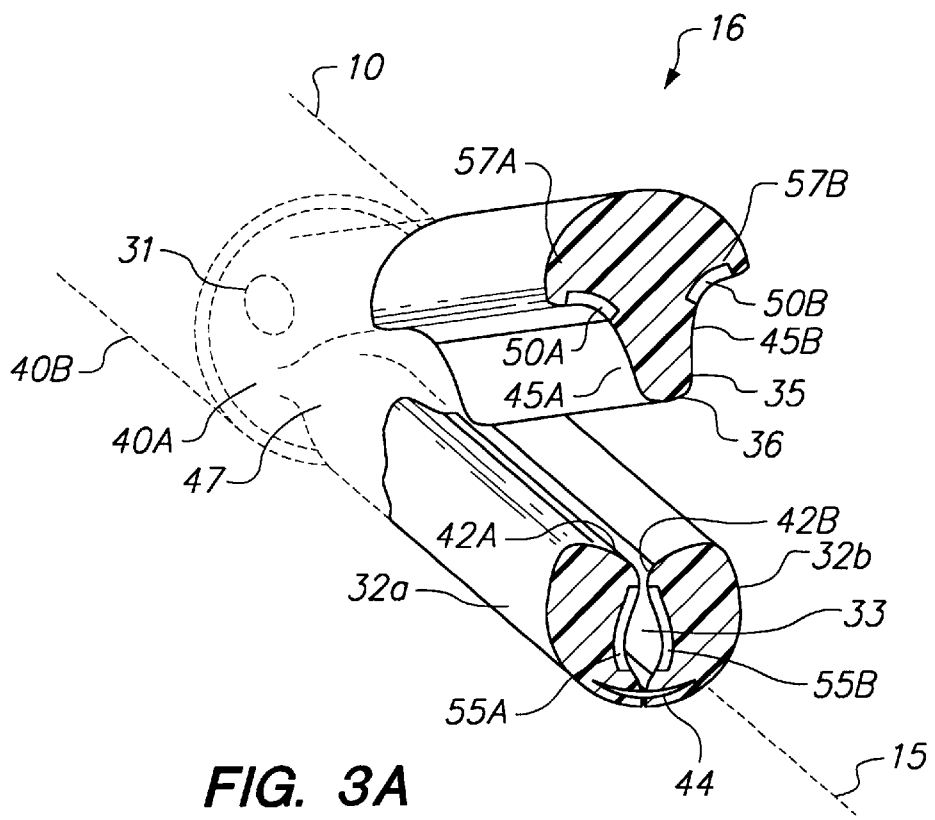
FIG. 3A is a perspective sectional view of the jaw structure of FIG. 2A.
Figure 3B:
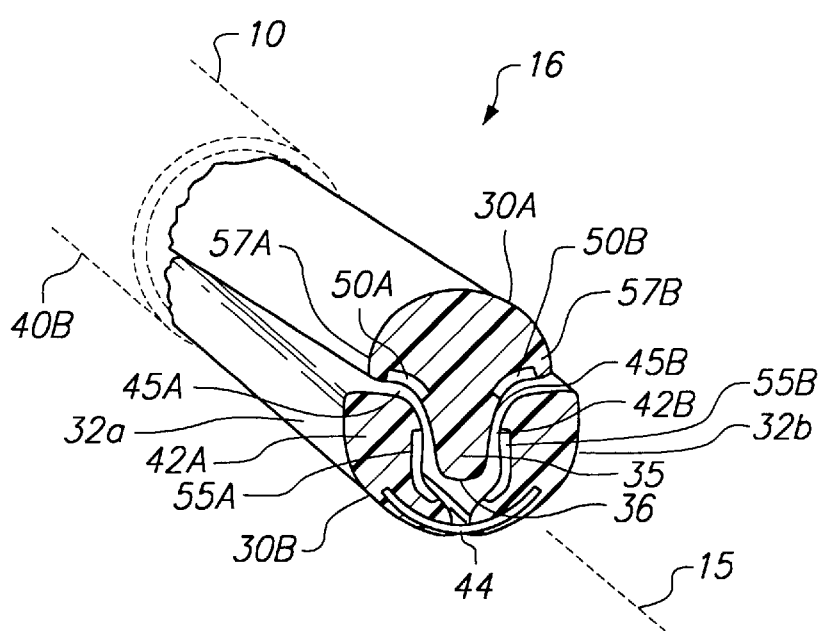
FIG. 3B is a perspective sectional view of the jaw structure of FIG. 2B.
Figure 4A:
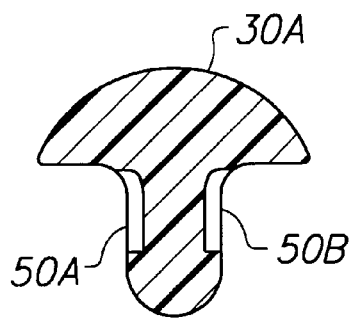
FIGS. 4A–4D depict alternative cross-sectional shapes of the upper jaw side of the device of the present invention.
Figure 4B:
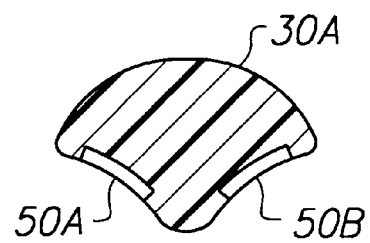
Figure 4C:
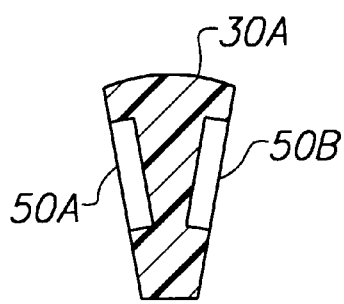
Figure 4D:
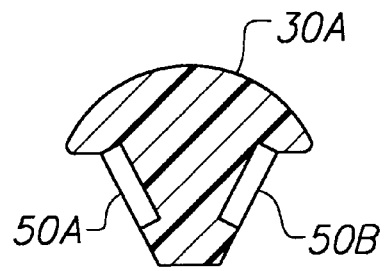

Referring now also to FIGS. 3A–3B, working end 16 comprises an openable/closeable jaw assembly with first and second jaw sides or members 30A and 30B carried by introducer portion 10. Upper jaw side 30A is pivotable around pin 31 and lower jaw side 30B is in an axially stationary position relative to the introducer member. Alternatively, both jaw arms or members 30A and 30B may be pivotable.

Lower jaw member 30B is configured as resilient structure with right-side and left-side jaw elements 32a and 32b defining space or gap 37 therebetween. The deflectable right-side and left-side elements 32a and 32b are adapted to at least partly straddle the centered projecting portion 35 of upper jaw side 30A when closing. Upper jaw member 30A is moveable relative to lower jaw member 30B from an open position (shown in FIGS. 2A and 3A) through various converging positions (not shown) towards the closed position of FIGS. 2B and 3B. Spring 33 biases jaw member 30A to the open position (see FIG. 2A and 2B).

Introducer portion 10 comprises concentric inner and outer extension members 40A and 40B. Lower jaw side 30B extends from inner extension member 40A and upper jaw side 30A is pivotably coupled to inner extension member 40A by pivot pin 31. Outer extension member 40B slidably cooperates with inner extension member 40A and serves as a jaw-actuation mechanism to slidably push the upper jaw toward a closed position (FIG. 2B). Alternatively, upper jaw 30A may be coupled to extension member 40A by any suitable form of resilient hinge-type element rather than pivot pin 31, such as a living hinge formed of plastic injection-molded material. Upper and lower jaw members 30A and 30B of working end 16 are of a medical grade plastic or other nonconductive material or are otherwise insulated from the RF electrodes carried within the jaw assembly which are described in more detail below.

Lower jaw side 30B comprises right-side jaw face portion 42A and left-side jaw face portion 42B on deflectable elements 32a and 32b, respectively, which elements are capable of deflecting or flexing rotationally relative to axis 15. Each right-side and left-side jaw face 42A and 42B optionally may have a grip texture 43 (not shown which may include serrations, hatching, projecting points, etc.) covering its vessel-engaging surface for gripping an engaged vessel.

As may be observed by comparing FIG. 3A and FIG. 3B, each of deflectable jaw elements 32a and 32b rotationally flexes about spring hinge element 44. Hinge element 44 may be a flat spring of any suitable resilient material, and urges the top edges of elements 32a and 32b inward toward axis 15. Alternatively, elements 32a and 32b may be pivotable relative to axis 15 by means of a pin-type hinge (not shown) with a spring urging the arm inward toward axis 15, rather than employing hinge element 44. Elements 32a and 32b are coupled to extension member 40A by resilient connections at 47 disposed in the distal end of extension member 40A. In a preferred embodiment, plastic elements 32a and 32b are engaged with insert-molded metal spring 44.

In operation, when right-side and left-side jaw faces 42A and 42B close toward the proximal-most edge 36 of cooperating projecting portion 35, and thereafter push against edge 36, deflectable elements 32a and 32b deflect rotationally outwardly. This movement of elements 32a and 32b in turn causes faces 42A and 42B to slide along right-side face 45A and left-side face 45B of projecting portion 35. The axial force required to be applied on extension member 40A to cause elements 32a and 32b to deflect around projecting portion 35 is not high, and is determined by the spring constant of the resilient material of spring 44.

The spring material of hinge element 44 preferably is selected to provide sufficient resistance to outward deflection of elements 32a and 32b to collapse a blood vessel and then to maintain a length of the captured vessel under pressure, thereby insuring the walls of the vessel lumen are in suitable contact for welding. Thus, cooperation of right-side and left-side faces 42A and 42B when sliding around right-side and left-side faces 45A and 45B of projecting portion 35 progressively engages the vessel, from its center outward, to squeeze blood from the lumen. Moreover, cooperation of right-side and left-side faces 42A and 42B when sliding around right and left-side faces 45A and 45B stretches the vessel section around projecting portion 35. The extent of such stretching or vessel elongation is partly dependent on the grip texture 43 (not shown) impressed on right-side and left-side faces 42A and 42B and the resistance to flexing engineered into hinge element 44 coupling elements 32a and 32b.

Referring still to FIGS. 3A and 3B, the cross sectional shape of projecting portion 35 has an arcuate shape with left-side and right-side face portions 45A and 45B that extend into gap 37 between elements 32a and 32b and the cooperating curved surfaces thereof. Cooperating faces 42A and 42B and 45A and 45B, respectively, may be have any suitable planar or curved cross-section relative to one another, and still squeeze the blood from the lumen as a blood vessel is collapsed. FIGS. 4A–4D depict alternative cross-sectional shapes of distal jaw side 30A of an openable/closeable jaws structure having projecting portion 35. The cooperating lower jaw side 30B (not shown) for the upper jaw 30A depicted in FIGS. 4A–4D would include a curved or linear mating surface for surfaces 45A and 45B.

Working end 16 carries an active and non-active electrode configuration that allows RF energy delivery at very low power levels, e.g., 0.50 to 30.0 watts, as described hereinbelow, yet still creates thermal effects in tissue sufficient to denature proteins. The electrode configuration performs a method of RF energy delivery referred to herein as "directed-path" bi-polar RF energy delivery. Such "directed-path" RF energy delivery is accomplished sing a "channeling" electrode system comprising at least one "non-active" electrode that is positioned in contact with the targeted tissue, but spaced apart and intermediate to the first and second "active" bi-polar electrodes.

In FIGS. 3A–3B, right-side and left-side faces 45A and 45B, respectively, of projecting portion 35 carry cooperating right-side and left-side active bi-polar electrodes 50A and 50B. As shown in FIGS. 2A and 2B, wires 62A and 62B carry bi-polar RF energy to and from the paired conductive electrodes 50A and 50B. Active electrodes 50A and 50B may comprise any suitable material, such as gold, nickel titanium, platinum, stainless steel, aluminum or copper, and may be molded or bonded to faces 45A and 45B of the upper jaw member. Channeling electrodes 55A and 55B are carried in right-side and left-side jaw faces 42A and 42B, respectively, that generally oppose jaws faces 45A and 45B carrying active electrodes 50A and 50B, respectively. Channeling electrodes 55A and 55B may comprise any suitable conductive material, but are not electrically active, i.e., they are entirely surrounded by non-conductive material, such as a plastic.

In accordance with the present invention, a channeling electrode may comprise a one or more such electrode. For example, hinge element 44 may comprise a channeling electrode, if in contact with tissue, and thus serve multiple functions. As described hereinbelow, any number of channeling electrodes may be used, provided that the channeling electrodes are proximate to one another and positioned to contact the targeted tissue between the active electrodes. The channeling electrodes of the present invention direct the path of bi-polar RF current flow at the desired low lower levels (0.50 to 30.0 watts).

The active electrode pair 50A and 50B are configured to send RF energy through a targeted longitudinal section of vessel captured in working end 16. While right-side and left-side electrodes 50A and 50B are illustratively carried by upper jaw member 30A, it will be appreciated that these electrodes may be carried in any left and right parts of working end 16 in contact with an engaged blood vessel for delivering RF current longitudinally through the vessel section. For example, the electrodes alternatively may be carried in right-side and left-side faces 42A and 42B of jaw elements 32a and 32b. The channeling electrode(s) may be arranged at any suitable position between the left and right active bi-polar electrodes.

Figure 5:
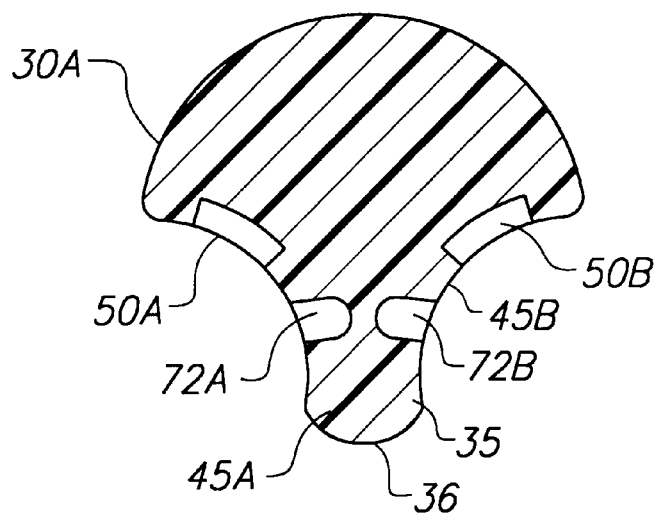
FIG. 5 shows an alternative upper jaw element having thermal sensors.

With respect to FIG. 5, an alternative embodiment is described that includes an array of individual sensors 72A and 72B carried in a portion of the jaw assembly that contacts the blood vessel section being welded. Sensors 72A–72B preferably are located slightly spaced apart from electrodes 50A and 50B, and measure temperatures of tissue adjacent to the active electrodes during a vessel welding operation. Alternatively, sensors 72A and 72B may be replaced by more or fewer sensors, and may be configured to measure the temperatures of the electrodes, rather than the adjacent tissue. Each sensor of an array preferably comprises a thermocouple, e.g., a T-type thermocouple formed from paired dissimilar metals such as copper and constantan, or a thermister (i.e., a temperature sensor that has a resistance that varies with the temperature level).

Figure 6B:
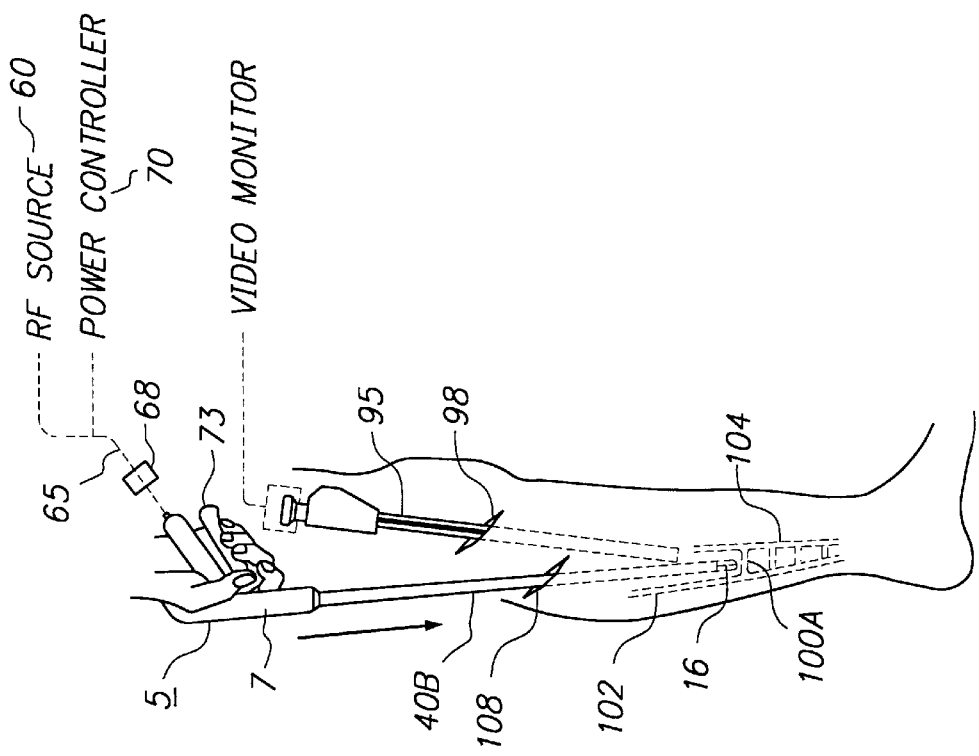
FIGS. 6A–6B are schematic views of a SEPS procedure performed using the instrument and methods of the present invention.
Figure 6A:
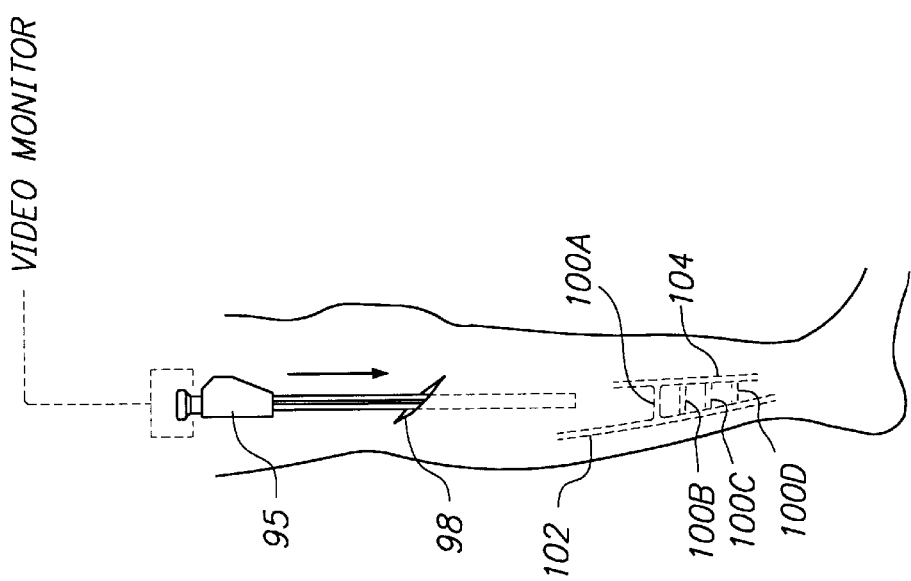

Referring now to FIGS. 6A–6B, RF source or generator 60 is provided for delivering RF current to active bi-polar electrodes 50A and 50B in contact with the blood vessel (or other vascularized tissue) engaged in the jaw assembly. As shown in FIG. 3B, the active and channeling electrodes are positioned in faces 45A–45B and 42A–42B so as to provide laterally outwardly directed insulated portions 57A and 57B of both jaw members, thereby insuring that the electrodes are not exposed on an outermost surface of working end 16 when the jaws are closed. Thus, the positioning of electrodes prevent them from contacting tissue surfaces other than the targeted vessel section.

Bi-polar wires 62A and 62B extend through handle portion 7 (see FIG. 6A) to power transmission cable 65, which is connected via a detachable coupling to an energy source, such as a previously known RF generator or source 60. Bi-polar RF current may be switched on and off by foot pedal 68, or any other suitable means such as a switch in handle 7 (not shown). Optional power controller 70, described in more detail hereinbelow, is coupled to instrument 5 and RF source 60 via cable 65. Lever arm 73 in handle 7 is arranged to move outer extension member 40B back and forth as a jaw-actuating mechanism, as is known in the art, to move upper jaw side 30A toward lower jaw side 30B between the open position (FIG. 2A) and the closed position (FIG. 2B).

Still referring to FIGS. 6A–6B, operation and use of the instrument of FIG. 2 in performing a method of the invention is described. First, the surgeon inserts endoscope 95 (or any other suitable instrument) into a patient's leg through first incision 98, to dissect an access path to perforator 100A between superficial vein 102 and deep vein 104. It should be appreciated that there may be from one to ten or more perforator vessels that must be sealed in a SEPS procedure, four perforators 100A–100D are shown. The surgeon then introduces the distal end of instrument 5 through second incision 108 and advances it towards the location of perforator 100A. The access space around the perforators may be dissected and retracted mechanically or by insufflation by known means (not shown).

Figure 7A:
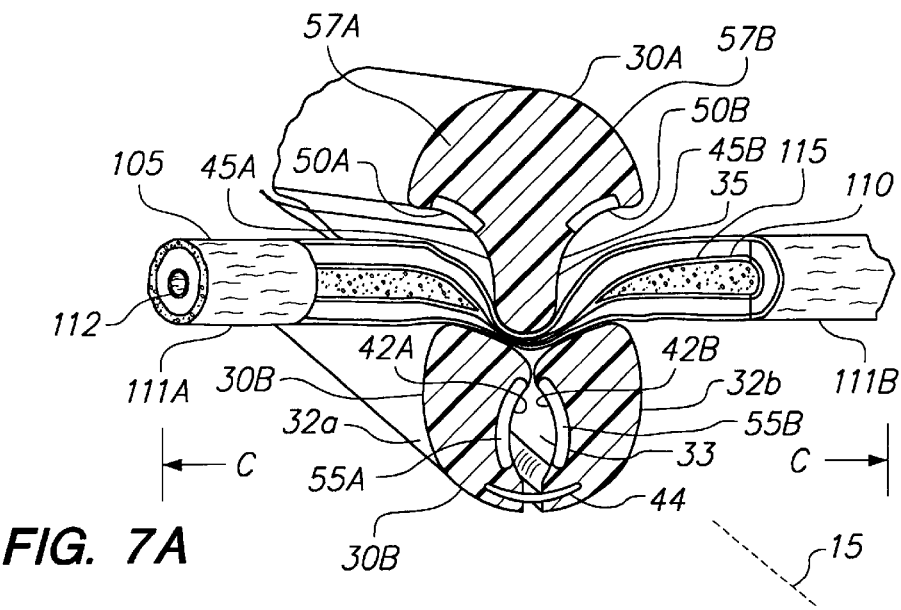
FIGS. 7A–7C are sectional views of a part of a blood vessel targeted for treatment depicting, in sequence, a method of the present invention to weld or seal the blood vessel lumen.

FIG. 7A is an enlarged view representing a particular longitudinal section 105 of perforator 100A (or any other blood vessel) that is targeted for sealing in the interior of the patient's body. The surgeon generally identifies a vessel section 105 which is bounded by left and right ends portions 111A and 111B and is positioned between upper and lower jaw members 30A and 30B in the open position. The vessel has lumen 110 and endothelium 112 with blood 115 within. Left and right ends 111A and 111B, respectively, of vessel 105 are spaced apart a distance C, as described further below.

Figure 7B:
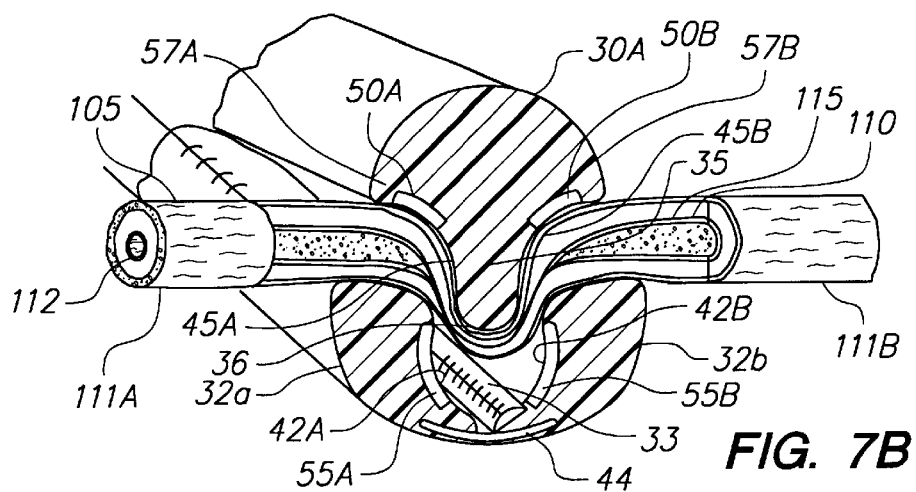

With respect to FIG. 7B, the surgeon progressively moves the jaws toward the closed position, so that right-side and left-side faces 42A and 42B of lower jaw side 30B press and collapse the vessel against proximal-most edge 36 of projecting portion 35. Thus, as lumen 110 is collapsed at a center portion of the targeted vessel section, flow of blood 115 through the vessel is pinched off and terminated.

Figure 7C:
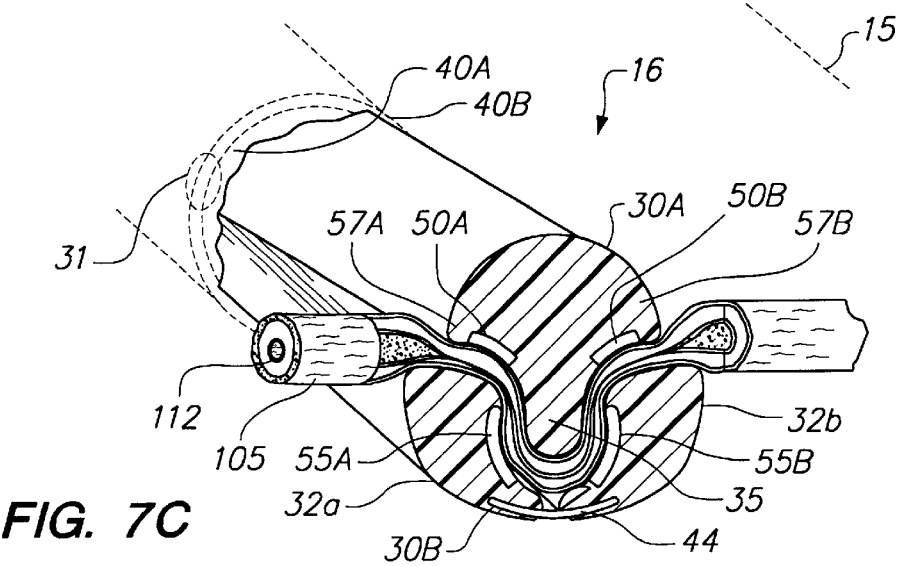

Referring next to FIGS. 7B and 7C, as vessel progressively collapses further, substantially all of the blood is squeezed from the vessel segment targeted for sealing. In particular, right-side and left-side jaw faces 42A and 42B carried by deflectable elements 32a and 32b of the lower jaw structure slidably move over the vessel relative to faces 45A and 45B of opposing jaw side 30A. In contrast to previously known jaw arrangements, which may trap blood between approximated vessel walls, the progressive sliding movement of portions of jaw faces 42A and 42B relative to the opposing jaw faces 45A and 45B causes substantially all blood 115 to be pushed out of the targeted vessel section. FIG. 7C shows the vessel section 105 captured in the jaw assembly in the closed position, ready for RF energy delivery.

Figure 8:
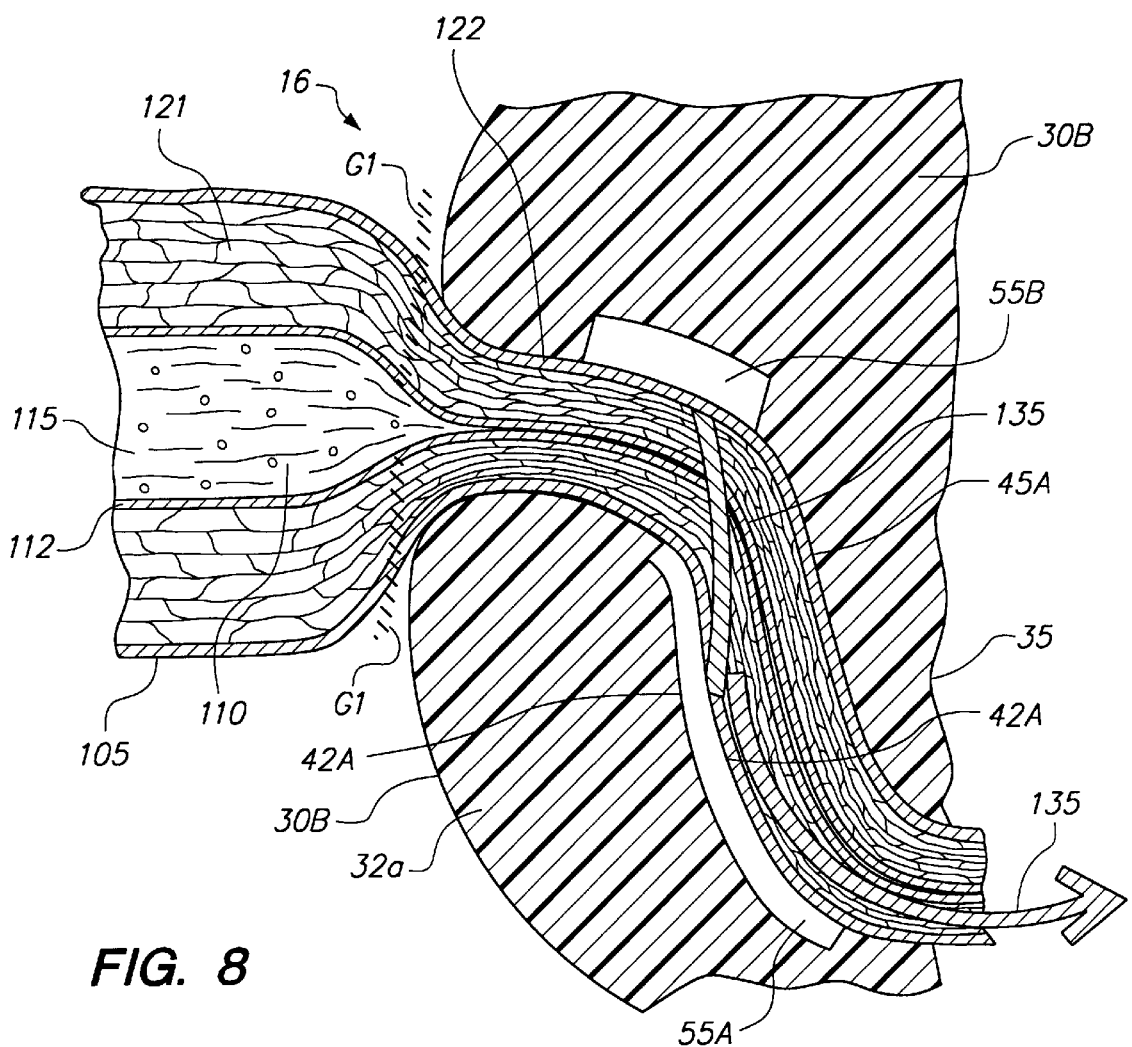
FIG. 8 is a sectional view of the targeted vessel section taken along line 8—8 of FIG. 7C.

Referring now to FIG. 8, an enlarged view of vessel section 105 is shown with RF current flow indicated by arrows 135. To weld or seal the target vessel section, the surgeon actuates a foot pedal or other type of switch to allow a bi-polar current to flow between electrodes 50A and electrode 50B longitudinally through the extended length C' of the vessel. The RF current flow along a path from the first bi-polar electrode, through the most conductive tissue, and to the cooperating second bi-polar electrode, i.e., along the path of least resistance between cooperating electrodes.

Applicant has discovered that by positioning channeling electrodes 55A and 55B intermediate to the active bi-polar electrodes 50A and 50B, RF current flow is channeled or directed between the active electrodes through the tissue in contact with the channeling electrodes. As illustrated in FIG. 8, arrows 135 (collectively) indicate the flow of RF current generally from first bi-polar electrode 50A through tissue toward channeling electrode 55A, then generally longitudinally through tissue proximate to channeling electrodes 55A and 55B, until reaching cooperating bi-polar electrode 50B.

Of particular interest to this method of the invention, it has been found that the use of the channeling electrode system substantially reduces "stray" RF current that finds its way along other paths of lesser resistance through tissues between electrodes. By thus directing RF current along a desired path through the tissue, along with the absence of stray RF flows, it has been observed that RF power levels can be reduced significantly and still deliver the required thermal effects needed to weld tissues.

Accordingly, the present invention provides a method of utilizing a working end 16 that has longitudinally spaced-apart bi-polar electrodes with at least one intermediate channeling electrode, is adapted to deliver RF current ranging in power from 0.50 to 30.0 watts for sealing lumens in organs, the power levels varying depending generally on the size of the vessel being sealed. More preferably, the method will deliver RF current ranging in power from 0.50 to 20.0 watts, and still more preferably, from 0.50 to 10.0 watts, to weld endothelial tissues or collagen containing tissues to create a thermal biological glue.

Referring still to FIG. 8, the schematic sectional illustration shows that an elongate weld 125 is created where the proteins (including collagen) are denatured, then intermix, and then fuse together upon cooling to fuse the vessel walls together. In delivering the flow of RF current generally between electrodes 50A and 50B along the path directed by channeling electrodes 55A–55B, the surgeon may select a pre-set current intensity levels. The duration of RF delivery may range from about 1.0 seconds to about 30.0 seconds or more depending on current intensity.

Returning to FIGS. 7A–7C, another aspect of the methods of the invention is described, in which the targeted vessel section is stretched or elongated as it is engaged by working end 16. In particular, targeted vessel section 105 is stretched somewhat lengthwise when right end 111A and left end 111B move apart, relative to the axis of the vessel. The premanipulated length of target section is indicated at C in FIG. 7A. The optional gripping texture 43 (not shown) of right-side and left-side faces 42A and 42B may assist in extending the vessel. It can be seen that the closing action of working end 16 causes projecting portion 35 to extend target vessel section 105 into gap 37 as deflectable elements 32a and 32b straddle projecting portion 35 to extend the vessel. FIG. 7C illustrates that the targeted vessel section is extended or lengthened somewhat to a length indicated at C' from the initial length indicated at C (FIG. 7A).

This aspect of longitudinally stretching or tensioning the vessel prior to RF delivery alters the impedance characteristics of the target tissue, thus enhancing RF energy delivery. Specifically, extension of the target vessel portion in FIG. 7C lowers the extracellular fluid (ECF) content of the vessel walls that are extended, thereby increasing the impedance (or resistance) of the tissue to RF current flow. Additionally, such stretching or tensioning may configured to provide a substantially uniform thickness of the target vessel, thereby ensuring a relatively uniform impedance over the length of the elongated, collapsed section of vessel.

Without limiting the method of the present invention to any particular theory, it is believed that the tissue extension or manipulation has the effect of (1) decreasing the ECF content level of the target vessel section 105 when calculated in terms of $ECF/cm^2$ of tissue mass, and (2) making the ECF level more evenly distributed throughout the targeted tissue (at the lower $ECF/cm^2$ level) whereas in the prior state, the ECF level could vary randomly within the cellular structure.

In FIG. 8, ECF in the non-extended tissue (indicated at 120) between cells 121 is altered to a different state in the extended tissue (indicated at 122), as the extracellular fluid is squeezed out of the tissue (this is indicted graphically by the varied patterns of cell density in FIG. 8, compare locations 120 and 122). In other words, a hydration gradient Gl is created between the tissue to be treated and the tissue outside the treatment area. In this way, the RF current generally flows through the extracellular matrix rather than passing through the intracellular fluids and cellular membranes.

The effects of the tissue manipulation caused by the extension of targeted vessel section 105 alternatively may be described as causing a "fuse" or "fuse point" to form in the tissue when subjected to the flow of RF current. Several advantages are offered by creating a fuse-type effect in the targeted tissue.

First, the delivery of RF current between electrodes 50A and 50B will deliver greater levels of thermal effects for a given current flow or intensity. Thus, the targeted tissue may be elevated to a particular desired temperature to denature proteins of endothelium 112 at lower levels of RF energy delivery. It is desirable to use lower levels, rather than higher levels, of RF current intensity which, it is believed, will reduce tissue charring, smoke and odor.

Second, the requisite temperature range for protein denaturation can be reached more quickly, thus speeding up the process of tissue welding. These first two advantages provide for an enhanced energy delivery profile (delivery of current intensity over several seconds).

Figure 1B:
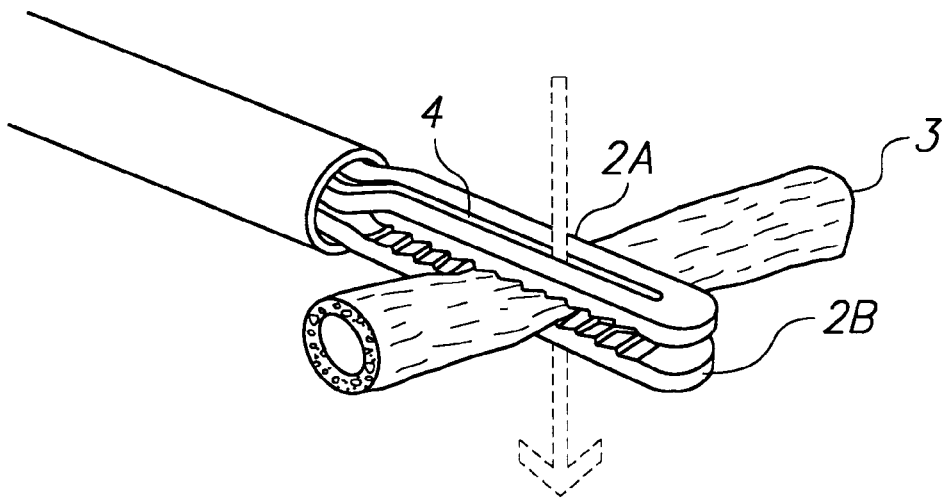

Third, the bi-polar flow longitudinally through the vessel between electrodes 50A to 50B naturally denatures proteins over a longer length of vessel lumen, thereby creating a more effective seal. This effect is not possible with typical prior art bi-polar devices that send current through pinched tissue between opposing jaw-electrodes (see FIG. 1B).

Fourth, it is believed that the uniformity in the ECF level in the target tissue allows for more uniform denaturation to provide a uniform biological glue.

Fifth, the bi-polar current flow longitudinally through the vessel provides little or no thermal spread outwardly along the vessel, since the RF current substantially flows along the path directed by the channeling electrodes between the paired "active" electrodes (and not outwardly). Also, the higher ECF level indicated at 120 in the vessel outwardly from vessel ends 111A and 111B, together with blood 115, acts as a heat sink to prevent significant outward thermal spread. In addition, the insulator portions of the working end 57A and 57B, outward of electrodes 50A and 50B, also prevent outward thermal spread.

Figure 9:
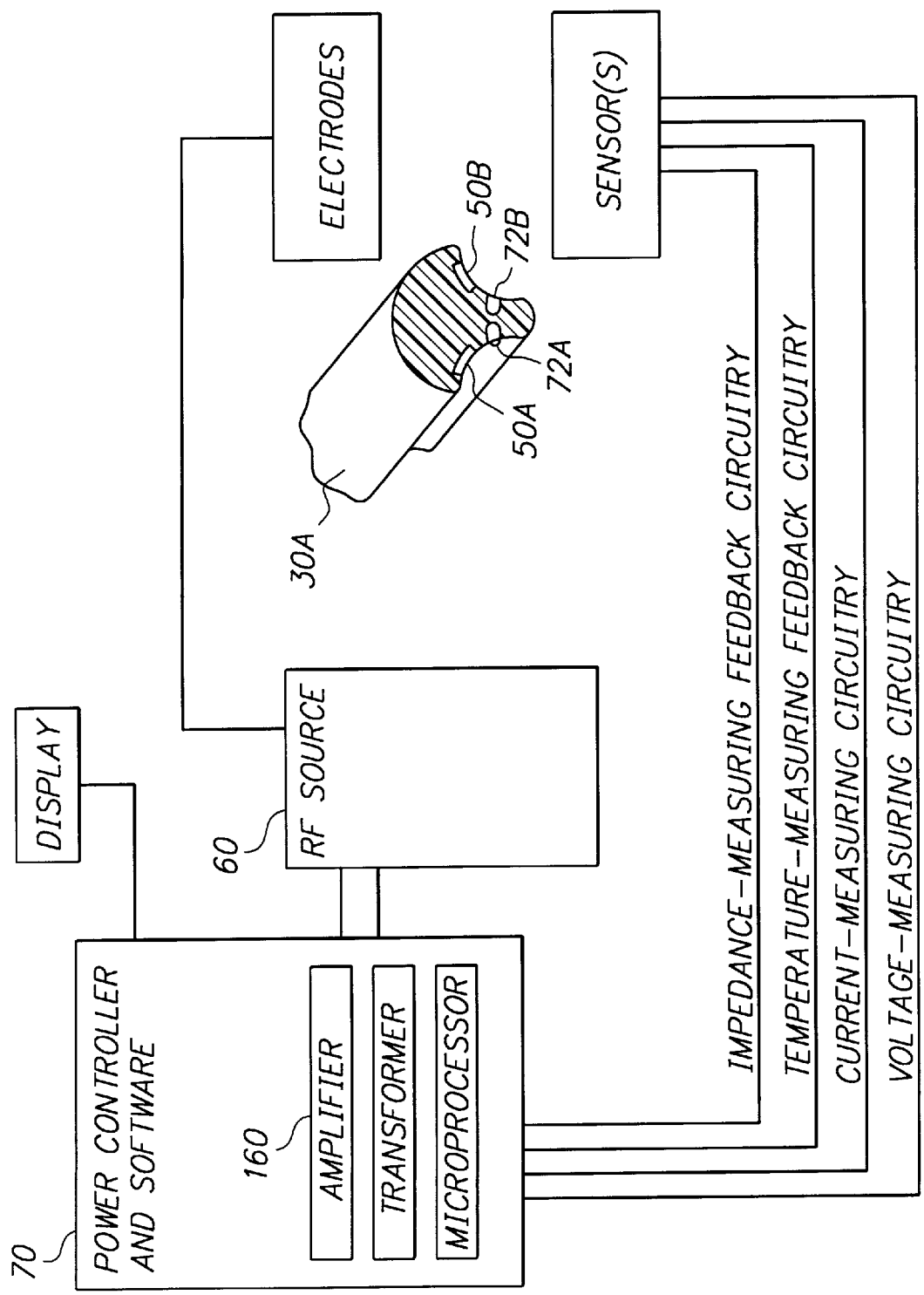
FIG. 9 is a block diagram of a power controller of an alternative embodiment of the apparatus of the present invention.

Referring now to FIG. 9, an alternative embodiment of the present invention is described that includes sensors 72A–72B carried by the working end 16 (as shown in FIG. 5) in combination with electronic ower controller 70 indicated in FIGS. 6A–6B. Sensors 72A–72B are adapted to send feedback signals to power controller 70, which modulates the delivery of RF energy delivery to the instrument. Power controller 70 is shown in FIG. 9 interconnecting RF source 60 and instrument 5.

Power controller 70 is adapted to control delivery of RF power in a bi-polar manner between paired electrodes 50A and 50B, as channeled by channeling electrodes 55A–55B according to predetermined parameters. The power controller 70 may be designed to selectively control power delivery to the electrodes in varied operational modes. The power controller 70, which typically includes microprocessor 160 together with appropriate software, may be programmed to deliver power according to preset parameters. On the power controller 70, there may be a keyboard, disk drive or other non-volatile memory system, and displays as are well known in the art for operating the system. Operator interface 162 may include various types of imaging systems for observing the RF treatment cycle such as thermal sensor displays and/or impedance monitoring displays.

In the preferred manner of operation or temperature-controlled operational mode, the operator selects a target temperature level, typically a known temperature at which proteins will denature in the targeted vessel lumen. Temperature signals measured by a sensor or sensor array 72A and 72B are continuously provided to power controller 70 through a feedback circuit. Power controller 70 is programmed to terminate power delivery after the targeted vessel section reaches a predetermined temperature for a sufficient period of time, e.g., from about 1.0 second to about 30.0 seconds, to denature proteins and form a biological glue but still not carbonize the tissue.

The temperature at the surface of the vessel in contact with the sensors is substantially close to the temperature within the lumen. RF power source 60 delivers RF current ranging in power at the aforementioned power levels for the time intervals above to reach (or maintain) tissue temperatures ranging between 65° C. and 95° C. to denature proteins in the (collagen-containing) endothelial tissues to form a biological glue. More preferably, the RF power source delivers RF current ranging under the aforementioned parameters to reach (or maintain) tissue temperatures ranging between 70° C. and 90° C., and still more preferably 75° C. and 85° C., to denature proteins in the endothelial tissues to form the biological glue.

As will be appreciated, the preferred embodiments described hereinabove are especially adapted to weld blood vessels. The principles of the present invention may be readily adapted to similar device (not shown) that further includes a reciprocating blade member, such as are known in the art for transecting welded blood vessels. Alternatively, a power controller may be included to modulate RF power delivery to the electrode array based on feedback from sensors as disclosed in co-pending U.S. Provisional Pat. application Ser. No. 60/074,808, filed Feb. 17, 1998, which is incorporated herein by reference.

The present invention may be readily adapted for use in sealing other organs or anatomic structures having a lumen surrounded by walls containing proteins, for example collagen, that may be denatured and intermixed to form a thermal biological glue. It is believed that most tubular organs in the body have walls that are capable of such RF welding utilizing the techniques disclosed herein. For example, various lumens in a patient's body may be sealed such intestines, ducts, and any other tubular organs or conduits in a patient's body.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. Apparatus for welding a vessel comprising:

a first member having a first vessel engaging surface;

a second member having a second vessel engaging surface, the second vessel engaging surface disposed in opposing relation to the first vessel engaging surface, the second member operatively coupled to the first member to progressively engage a portion of the vessel disposed between the first and second members to squeeze fluid out and define an engagement plane;

first and second bi-polar electrodes disposed in spaced apart relation on one of the first and second members and adapted to be in communication with the engagement plane, the first and second bi-polar electrodes adapted to be coupled to a source of RF energy to provide a flow of current between the first and second bi-polar electrodes; and a channeling electrode disposed on one of the first and second members at a location at least partially intermediate the first and second bi-polar electrodes and adapted to be in communication with the engagement plane, the channeling electrode adapted to direct the flow of current between the first and second bi-polar electrodes through a portion of vessel in contact with the channeling electrode.

2. The apparatus of claim 1 wherein the engagement plane defines a curvilinear surface.

3. The apparatus of claim 1 wherein the first member forms a mating surface to the second member.

4. The apparatus of claim 3 wherein the first and second members comprise first and second opposing jaw members, respectively.

5. The apparatus of claim 4 further comprising an actuation mechanism for moving at least one of the first and second opposing jaw members towards and away from the other.

6. The apparatus of claim 5 wherein the second jaw member comprises right and left lateral portions, the right and left lateral portions deflecting outwardly away from one another to elongate the engagement plane when the first jaw member engages the second jaw member.

7. The apparatus of claim 6 further comprising a hinge element that maintains the right and left lateral portions of the second jaw member in contact with the first jaw member when the first jaw member contacts the second jaw member.

8. The apparatus of claim 4 wherein the first and second bi-polar electrodes are disposed on the first jaw member and the channeling electrode is disposed on the second jaw member.

9. The apparatus of claim 1 further comprising a sensor disposed on one of the first and second members.

10. The apparatus of claim 9 wherein the sensor is a temperature sensor, the apparatus further comprising an RF power controller that modulates the RF energy responsive to an output of the temperature sensor.

11. A method for welding a vessel comprising:

identifying a vessel to be sealed, the vessel having first and second ends;

grasping the vessel at the first and second ends;

contacting first and second bi-polar electrodes to the vessel in spaced apart relation;

contacting a channeling electrode to a portion of the vessel at a location at least partially intermediate the first and second electrodes;

collapsing an intermediate portion of the vessel to progressively engage the intermediate Portion to squeeze fluid out and approximate opposing walls of the vessel; and applying an RF current between the first and second electrodes so that the RF current flows through and welds the portion of the vessel in contact with the channeling electrode.

12. The method of claim 11 wherein the RF current is applied at power of less than 30 watts.

13. The method of claim 11 further comprising longitudinally extending the intermediate portion of the vessel located between the first and second ends to alter an impedance of the intermediate portion.

14. The method of claim 13 wherein longitudinally extending the intermediate portion of the vessel further comprises reducing an extracellular fluid content of the vessel.

15. The method of claim 13 wherein longitudinally extending the intermediate portion of the vessel further comprises reducing the intermediate portion to a substantially uniform thickness.

16. The method of claim 15 wherein longitudinally extending an intermediate portion of the vessel to alter an impedance of the intermediate portion further comprises making the impedance of the intermediate portion substantially uniform.

17. The method of claim 11 wherein progressively engaging the intermediate portion of the vessel further comprises squeezing the vessel longitudinally outward from a central location of the intermediate portion so that substantially no fluid is entrapped when approximating the opposing vessel walls.

18. The method of claim 11 further comprising contacting a sensor to the intermediate portion of the vessel.

19. The method of claim 18 wherein the sensor monitors temperature of the intermediate portion of the vessel and generates an output signal, the method further comprising modulating the RF current applied to the intermediate portion responsive to the output signal.

20. The method of claim 19 further comprising modulating the RF current applied to the intermediate portion to prevent a preselected temperature value from being exceeded.

* * * * *